(12) United States Patent
Park et al.

(10) Patent No.: US 12,121,335 B2
(45) Date of Patent: Oct. 22, 2024

(54) APPARATUS AND METHOD FOR ESTIMATING BLOOD PRESSURE

(71) Applicant: SAMSUNG ELECTRONICS CO., LTD., Suwon-si (KR)

(72) Inventors: Chang Soon Park, Chungju-si (KR); Ui Kun Kwon, Hwaseong-si (KR); Young Soo Kim, Seoul (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 315 days.

(21) Appl. No.: 17/580,312

(22) Filed: Jan. 20, 2022

(65) Prior Publication Data
US 2022/0233079 A1 Jul. 28, 2022

(30) Foreign Application Priority Data

Jan. 25, 2021 (KR) .................. 10-2021-0010249
Sep. 1, 2021 (KR) .................. 10-2021-0116334

(51) Int. Cl.
*A61B 5/021* (2006.01)
*A61B 5/00* (2006.01)
(Continued)

(52) U.S. Cl.
CPC .......... *A61B 5/021* (2013.01); *A61B 5/02416* (2013.01); *A61B 5/029* (2013.01); *A61B 5/7239* (2013.01); *A61B 2560/0223* (2013.01)

(58) Field of Classification Search
CPC ..... A61B 5/021; A61B 5/02416; A61B 5/029; A61B 5/7239; A61B 2560/0223; A61B 5/02108
See application file for complete search history.

(56) References Cited

U.S. PATENT DOCUMENTS

| 8,574,162 B2 | 11/2013 | Watson |
| 10,045,701 B2 | 8/2018 | Schecter |

(Continued)

FOREIGN PATENT DOCUMENTS

| KR | 10-1503604 B1 | 3/2015 |
| KR | 10-2018-0010062 A | 1/2018 |

(Continued)

OTHER PUBLICATIONS

Lin, Wan-Hua et al., "Towards accurate estimation of cuffless and continuous blood pressure using multi-order derivative and multi-variate photoplethysmogram features", Biomedical Signal Processing and Control, vol. 63, Sep. 18, 2020. (12 pages total).

(Continued)

*Primary Examiner* — Hien N Nguyen
(74) *Attorney, Agent, or Firm* — Sughrue Mion, PLLC

(57) ABSTRACT

An apparatus for estimating blood pressure is provided. The apparatus for estimating blood pressure according to an example embodiment includes: a sensor configured to measure a photoplethysmogram (PPG) signal from an object; and a processor configured to detect a position of a dicrotic notch based on a local maximum point and a local minimum point of a second-order derivative signal of the PPG signal, to obtain a first value and a second value from a first section and a second section of the PPG signal divided based on the dicrotic notch of the PPG signal, to obtain a pulse pressure feature value based on the first value and the second value, and to estimate blood pressure based on a variation in the obtained pulse pressure feature value compared to a reference pulse pressure feature value.

15 Claims, 13 Drawing Sheets

(51) Int. Cl.
  *A61B 5/024* (2006.01)
  *A61B 5/029* (2006.01)

(56) References Cited

U.S. PATENT DOCUMENTS

| | | | |
|---|---|---|---|
| 10,165,953 | B2 | 1/2019 | Addison et al. |
| 10,716,518 | B2 | 7/2020 | Basu et al. |
| 11,172,891 | B2 | 11/2021 | Aung et al. |
| 2012/0259189 | A1* | 10/2012 | Cohen ............... A61B 8/065 600/528 |
| 2015/0196209 | A1 | 7/2015 | Morris et al. |
| 2015/0327785 | A1* | 11/2015 | Lading ............... A61B 5/7278 600/480 |
| 2016/0270668 | A1 | 9/2016 | Gil |
| 2017/0215749 | A1* | 8/2017 | Zhuo ............... A61B 5/02055 |
| 2018/0020990 | A1 | 1/2018 | Park et al. |
| 2020/0054290 | A1* | 2/2020 | Jang ............... A61B 5/1102 |
| 2020/0107789 | A1* | 4/2020 | Kwon ............... A61B 5/029 |
| 2020/0113453 | A1* | 4/2020 | Park ............... A61B 5/02108 |
| 2020/0113526 | A1 | 4/2020 | Park et al. |
| 2020/0221960 | A1* | 7/2020 | Jang ............... A61B 5/7242 |
| 2020/0275839 | A1 | 9/2020 | Park et al. |
| 2020/0288985 | A1* | 9/2020 | Robinson ............... A61B 5/1126 |
| 2020/0390347 | A1 | 12/2020 | Vallee |
| 2021/0100456 | A1 | 4/2021 | Park et al. |
| 2021/0401332 | A1 | 12/2021 | John et al. |

FOREIGN PATENT DOCUMENTS

| | | |
|---|---|---|
| KR | 10-2020-0021208 A | 2/2020 |
| KR | 10-2020-0041680 A | 4/2020 |
| KR | 10-2020-0077256 A | 6/2020 |
| KR | 10-2020-0105212 A | 9/2020 |
| WO | 2016/130083 A1 | 8/2016 |
| WO | 2020/099218 A1 | 5/2020 |

OTHER PUBLICATIONS

Li, Yanjun et al., "Characters available in photoplethysmogram for blood pressure estimation: beyond the pulse transit time", Australasian Physical and Engineering Sciences in Medicine, vol. 37, No. 2, Apr. 11, 2014, pp. 367-376. (10 pages total).

Communication issued Jun. 20, 2022 by the European patent Office in European Patent Application No. 22153018.1.

Youngzoon Yoon et al., "Nonconstrained Blood Pressure Measurement by Photoplethysmography", Journal of the Optical Society of Korea, vol. 10, No. 2, Jun. 2006, 5 pages total.

Sandrine C. Millasseau et al., "The Vascular Impact of Aging and Vasoactive Drugs: Comparison of Two Digital Volume Pulse Measurements", the American Journal of Hypertension, Ltd., vol. 16, No. 6, Jun. 2003, 6 pages total.

Martin C Baruch et al., "Validation of the pulse decomposition analysis algorithm using central arterial blood pressure", BioMedical Engineering OnLine, 13, 96, 2014, 19 pages total.

\* cited by examiner

APPARATUS AND METHOD FOR ESTIMATING BLOOD PRESSURE

CROSS-REFERENCE TO RELATED APPLICATION(S)

This application claims priority from Korean Patent Application No. 10-2021-0010249, filed on Jan. 25, 2021, and Korean Patent Application No. 10-2021-0116334, filed on Sep. 1, 2021, in the Korean Intellectual Property Office, the entire disclosures of which are herein incorporated by reference for all purposes.

BACKGROUND

1. Field

The disclosure relates to technology for estimating blood pressure, and more particularly to technology for estimating blood pressure using dicrotic notch.

2. Description of the Related Art

Recently, with the aging population, soaring medical costs, and a lack of medical personnel for specialized medical services, research is being actively conducted on information technology (IT)-medical convergence technologies, in which IT technology and medical technology are combined. Particularly, monitoring of the health condition of the human body is not limited to medical institutions, but is expanding to mobile healthcare fields that may monitor a user's health condition anywhere and anytime in daily life at home or office. Examples of bio-signals, indicating the health condition of individuals, include an electrocardiography (ECG) signal, a photoplethysmogram (PPG) signal, an electromyography (EMG) signal, etc., and various bio-signal sensors have been developed to measure these signals in daily life. Particularly, a PPG sensor may estimate blood pressure of a human body by analyzing a shape of pulse waves which reflect cardiovascular status and the like.

According to studies on the PPG signal, the entire PPG signal is a summation of a propagation wave propagating from the heart to peripheral parts of the body and reflection waves returning from the peripheral parts. Further, it has been known that information for estimating blood pressure may be obtained by extracting various features associated with the propagation wave or the reflection waves.

SUMMARY

According to an aspect of an example embodiment, provided is a an apparatus for estimating a blood pressure, the apparatus including: a sensor configured to obtain a photoplethysmogram (PPG) signal from an object; and a processor configured to: detect a position of a dicrotic notch based on a local maximum point and a local minimum point of a second-order derivative signal of the PPG signal; obtain a first value and a second value from a first section and a second section of the PPG signal divided based on the dicrotic notch of the PPG signal; obtain a pulse pressure feature value based on the first value and the second value; and estimate a blood pressure based on a variation in the obtained pulse pressure feature value compared to a reference pulse pressure feature value.

The processor may be configured to determine pairs of local maximum points and local minimum points of the second-order derivative signal of the PPG signal, and detect the position of the dicrotic notch based on, for each pair of the pairs of the local maximum points and the local minimum points, a difference between a second-order derivative value at the local maximum point and a second-order derivative value at the local minimum point.

The processor may be configured to detect, as the position of the dicrotic notch, a time point of a local maximum point of a pair, having a largest difference between the second-order derivative value at the local maximum point and the second-order derivative value at the local minimum point.

The processor may be configured to control to request a user to remeasure the PPG signal, based on a number of the determined pairs of the local maximum points and the local minimum points of the second-order derivative signal of the PPG signal being less than or equal to a predetermined number, or based on a largest difference between the second-order derivative value at the local maximum point and the second-order derivative value at the local minimum point among the pairs of the local maximum points and the local minimum points being less than or equal to a threshold value.

The processor may be configured to determine, as a reference time, at least one of a period of the PPG signal, or a time from a start point of the period of the PPG signal to a first local minimum point of the second-order derivative signal of the PPG signal, and set a time range to detect the position of the dicrotic notch based on the determined reference time.

The processor may be configured to set a start point of the time range to a value, obtained by multiplying the reference time by a first constant, and set an end point of the time range to a value, obtained by multiplying the reference time by a second constant.

The pulse pressure feature value may include a ratio between the first value and the second value.

The first value and the second value may include at least one of an area of the PPG signal in each corresponding section, a measurement time of each corresponding section, amplitude data of the PPG signal in each corresponding section, or an intensity of an nth (n being an integer equal to or greater than 1) order derivative signal of the PPG signal in each corresponding section.

The first value and the second value may include the amplitude data of the PPG signal, the amplitude data including at least one of a maximum amplitude value of the PPG signal in each corresponding section, a mean amplitude value of the PPG signal in each corresponding section, or a maximum value or a mean value of values obtained by raising PPG signal amplitudes to the power of n in each corresponding section.

The first value and the second value may include the intensity of the nth order derivative signal of the PPG signal, which is a sum of absolute amplitude values in the nth order derivative signal of the PPG signal in each corresponding section.

The processor may be configured to: estimate a pulse pressure based on the variation, and a reference pulse pressure obtained at a calibration time; extract a mean arterial pressure (MAP) feature value from the PPG signal, and estimate an MAP based on the extracted MAP feature value; and estimate a systolic blood pressure (SBP) or a diastolic blood pressure (DBP) based on the estimated MAP and the estimated pulse pressure.

The processor may be configured to estimate an SBP or a DBP based on a variation in an MAP at a time of blood pressure estimation compared to a reference MAP value at the calibration time, a variation in pulse pressure at the time of blood pressure estimation compared to a reference pulse pressure at the calibration time, and a reference SBP value or a reference DBP value at the calibration time.

The processor may be configured to: obtain the variation in the pulse pressure, based on the variation in the obtained pulse pressure feature value compared to the reference pulse pressure feature value; and obtain the variation in the MAP, based on a variation in an extracted MAP feature value compared to a reference MAP feature value.

The processor may be configured to estimate the SBP or the DBP based on the variation in the obtained pulse pressure feature value compared to the reference pulse pressure feature value, a variation in a cardiac output (CO) feature value compared to a reference CO feature value, and a variation in a total peripheral resistance (TPR) feature value compared to a reference TPR feature value.

According to an aspect of an example embodiment, provided is a method of estimating blood pressure, the method including: measuring a photoplethysmogram (PPG) signal from an object; obtaining a second-order derivative signal of the PPG signal; detecting a position of a dicrotic notch based on a local maximum point and a local minimum point of the second-order derivative signal of the PPG signal; obtaining a first value and a second value from a first section and a second section of the PPG signal divided based on the dicrotic notch of the PPG signal; obtaining a pulse pressure feature value based on the first value and the second value; and estimating blood pressure based on a variation in the obtained pulse pressure feature value compared to a reference pulse pressure feature value.

The detecting the position of the dicrotic notch may include: determining pairs of local maximum points and local minimum points of the second-order derivative signal of the PPG signal; and detecting the position of the dicrotic notch based on, for each pair of the pairs of the local maximum points and the local minimum points, a difference between a second-order derivative value at the local maximum point and a second-order derivative value at the local minimum point.

The detecting the position of the dicrotic notch may include detecting, as the position of the dicrotic notch, a local maximum point of a pair, having a largest difference between the second-order derivative value at the local maximum point and the second-order derivative value at the local minimum point.

The method may further include controlling to request a user to remeasure the PPG signal, based on a number of the determined pairs of the local maximum points and the local minimum points of the second-order derivative signal of the PPG signal being less than or equal to a predetermined number, or based on a largest difference between the second-order derivative value at the local maximum point and the second-order derivative value at the local minimum point among the pairs of the local maximum points and the local minimum points being less than or equal to a threshold value.

The method may further include determining, as a reference time, at least one of a period of the PPG signal, or a time from a start point of the period of the PPG signal to a first local minimum point of the second-order derivative signal of the PPG signal, and setting a time range to detect the position of the dicrotic notch based on the determined reference time.

The obtaining the pulse pressure feature value may include obtaining a ratio between the first value and the second value as the pulse pressure feature value.

BRIEF DESCRIPTION OF THE DRAWINGS

The above and/or other aspects will become apparent and more readily appreciated from the following description of example embodiments, taken in conjunction with the accompanying drawings in which.

DETAILED DESCRIPTION

Figure 1:
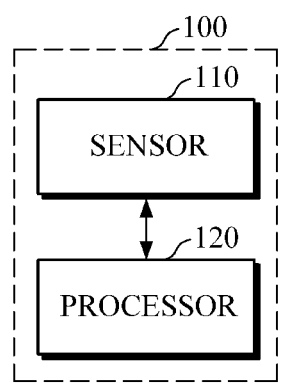
FIG. 1 is a block diagram illustrating an apparatus for estimating blood pressure according to an example embodiment.

Details of example embodiments are included in the following detailed description and drawings. Advantages and features of the example embodiments, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit for performing at least one function or operation and that may be embodied as hardware, software, or a combination thereof.

Hereinafter, embodiments of an apparatus and method for estimating blood pressure will be described in detail with reference to the accompanying drawings.

FIG. 1 is a block diagram illustrating an apparatus for estimating blood pressure according to an example embodiment.

Various embodiments of an apparatus 100 for estimating blood pressure may be mounted in a terminal, such as a smartphone, a tablet PC, a desktop computer, a laptop computer, a wearable device, and the like. In this case, the wearable device may be implemented as a wristwatch-type wearable device, a bracelet-type wearable device, a wristband-type wearable device, a ring-type wearable device, a glasses-type wearable device, a headband-type wearable device, or the like, but the wearable device is not limited thereto and may be mounted in various types of hardware devices, e.g., devices manufactured for use in specialized medical institutions.

Referring to FIG. 1, the apparatus 100 for estimating blood pressure includes a sensor 110 and a processor 120.

The sensor 110 may measure at least one bio-signal from a user's object. The bio-signal may be, for example, a photoplethysmogram (PPG) signal. The sensor 110 may measure other bio-signals, such as an electrocardiography (ECG) signal and the like.

In an example, the object may be an area on a wrist that is adjacent to a radial artery, an upper portion of the wrist where veins or capillaries are located, or peripheral parts of the body, such as fingers, toes, and the like where blood vessels are densely located.

The sensor 110 may include a light source for emitting light onto the object and a detector for detecting light emanating from the object when light, emitted onto the object by the light source, is scattered or reflected from body tissue of the object. The light source may include at least one of a light emitting diode (LED), a laser diode (LD), and a phosphor, but is not limited thereto. There may be one or more light sources. For example, the light source may include an LED array. The detector may include a photodiode, a photo transistor, a photodiode array, a photo transistor array, an image sensor (e.g., CMOS image sensor), and the like.

The sensor 110 may further include an additional component to be used for measuring bio-signals. For example, the sensor 110 may further include an amplifier for amplifying an electrical signal output from the detector that detects light, an analog/digital converter for converting an electrical signal output from the detector or an electrical signal output from the amplifier into a digital signal, and the like. In addition, if the sensor 110 measures the ECG signal, a plurality of electrodes may be included in the sensor 110. The following description will be given using the PPG signal as an example of the bio-signal, but the embodiment is not limited thereto.

The processor 120 may be connected to the sensor 110 electrically or mechanically or by wired or wireless communication. The processor 120 may control the sensor 110 and may receive the PPG signal from the sensor 110.

Upon receiving the PPG signal, the processor 120 may perform preprocessing such as filtering for removing noise, amplifying the PPG signal, and the like. For example, upon receiving the PPG signal, the processor 120 may perform band-pass filtering between 0.4 Hz to 10 Hz by using a band-pass filter, to remove noise from the PPG signal received from the sensor 110. The band-pass filter may be a digital filter implemented with software code. In another example, the band-pass lifter may be an analog filter, in which case the PPG signal measured by the sensor 110 may be transmitted to the processor 120 after passing through the band-pass filter.

In addition, the processor 120 may correct the PPG signal by reconstructing the PPG signal based on Fast Fourier Transform. However, the preprocessing is not limited thereto, and the processor 120 may perform various other preprocessing operations according to various measurement environments, such as computing performance or measurement accuracy of a device, purpose of blood pressure or pulse pressure estimation, a measured portion of a user, temperature and humidity of an object, temperature of the sensor, and the like.

The processor 120 may generate a representative pulse of the PPG signal measured by the sensor 110. The PPG signal includes repetitive pulses associated with a change in an amount of blood flowing through blood vessels, and the pulses may have slightly different shapes.

For example, the processor 120 may obtain an ensemble average of the plurality of pulses as the representative pulse. In another example, the processor 120 may determine a pulse, having a highest Signal to Noise Ratio (SNR) among the plurality of pulses, to be the representative pulse. However, the representative pulse is not limited thereto, and various embodiments of determining the representative pulse may be provided.

In this case, the processor 120 may determine the representative pulse after removing noise from the PPG signal as described above. The processor 120 may obtain cardiovascular features by using the representative pulse. In the following description, the PPG signal, used by the processor 120 to obtain feature values associated with blood pressure, may indicate the representative pulse of the PPG signal.

The processor 120 may estimate pulse pressure based on the PPG signal, and may estimate blood pressure based on the estimated pulse pressure. For example, the processor 120 may obtain a second-order derivative signal by taking second-order derivative of the PPG signal, and may obtain a feature value associated with pulse pressure (hereinafter referred to as a pulse pressure feature value) based on a local maximum point and a local minimum point of the obtained second-order derivative signal.

For example, the processor 120 may detect a position of a dicrotic notch in the PPG signal based on the local maximum point and the local minimum point of the second-order derivative signal, and may obtain the pulse pressure feature value based on the detected position of the dicrotic notch.

For example, the processor 120 may determine pairs of the local maximum points and the local minimum points in a predetermined time range of the second-order derivative signal of the PPG signal. Among the plurality of local maximum points and local minimum points, a local maximum point and a local minimum point which are adjacent to each other may be determined as a pair of the local maximum point and the local minimum point. In addition, the processor 120 may calculate an amplitude difference between the local maximum point and the local minimum point for each of the determined pairs of the local maximum points and the local minimum points, and may detect the position of the dicrotic notch based on the amplitude difference. For example, in a pair having a largest amplitude difference between the local maximum point and the local minimum point, the processor 120 may detect a time point of the local maximum point as the position of the dicrotic notch, but the position of the dicrotic notch is not limited thereto.

The processor 120 may set a predetermined time range to detect the dicrotic notch, and may detect the dicrotic notch within the set time range. The processor 120 may set the time range to detect a position of the dicrotic notch by multiplying a reference time by a predefined constant. In this case, the reference time may include a period of the PPG signal, a time up to a first local minimum point of the second-order derivative signal of the PPG signal, etc., but is not limited thereto.

The processor 120 may obtain a first value and a second value from both sections of the PPG signal divided based on the detected position of the dicrotic notch of the PPG signal, and may obtain the pulse pressure feature value based on the first value and the second value.

With respect to the both sections divided based on the position of the dicrotic notch of the PPG signal, the processor 120 may obtain, as the first value or the second value, any one or a combination of two or more of an area of the PPG signal in each section, a measurement time of each section, amplitude data of the PPG signal in each section, and an intensity of an nth (n being an integer equal to or greater than 1) order derivative signal of the PPG signal in each section.

For example, the processor 120 may divide the PPG signal into a first section (or a left section) and a second section (or a right section) based on the position of the dicrotic notch, and may obtain an area of each section by adding magnitudes of sampled amplitudes in a time domain of a corresponding section. However, the area of the PPG signal is not limited thereto, and the processor 120 may obtain the first value and the second value by using a partial area in a predetermined time range of each section as the area of the PPG signal, or the processor 120 may obtain the first value and the second value by calculating values by raising respective amplitudes, sampled when the PPG signal is acquired, to the power of n; adding the calculated values in the time domain of each section; and by using the added values as the area of the PPG signal.

In another example, the processor 120 may obtain the first value and the second value by determining, as amplitude data, any one of a maximum amplitude value of the PPG signal in each of both sections, divided based on the position of the dicrotic notch of the PPG signal, a mean amplitude value of the PPG signal in the respective sections, a maximum value of the values calculated by raising the PPG signal amplitudes to the power of n in the respective sections, and a mean value of the values calculated by raising the PPG signal amplitudes to the power of n in the respective sections, but is not limited thereto.

In yet another example, the processor 120 may determine the first value and the second value by determining, as an intensity of the nth order derivative signal of the PPG signal, a sum of absolute amplitude values in a signal, obtained by taking the nth order derivative of the PPG signal in the respective sections, but the first and second values are not limited thereto.

The processor 120 may obtain a ratio between the first value and the second value as a pulse pressure feature value, but the pulse pressure feature value is not limited thereto, and the processor 120 may obtain a difference, addition, or multiplication between the first value and the second value, or a combination thereof, or any value obtained based on the first value and the second value as the pulse pressure feature value.

The processor 120 may estimate pulse pressure by using the pulse pressure feature value. For example, the processor 120 may estimate pulse pressure by inputting the pulse pressure feature value into a pre-defined pulse pressure estimation model.

The processor 120 may estimate a user's mean arterial pressure (MAP) by extracting a feature value associated with MAP (hereinafter referred to as a MAP feature value) from the measured PPG signal. The MAP feature value may be obtained by a linear or non-linear combination of a feature value associated with cardiac output (CO) (hereinafter referred to as a CO feature value) and a feature value associated with total peripheral resistance (TPR) (hereinafter referred to as a TPR feature value).

The processor 120 may estimate a user's systolic blood pressure (SBP) or diastolic blood pressure (DBP) based on the measured PPG signal. In this case, the processor 120 may estimate the user's systolic blood pressure or diastolic blood pressure based on the obtained pulse pressure feature value. For example, the processor 120 may estimate the user's systolic blood pressure or diastolic blood pressure based on the estimated pulse pressure and the estimated MAP of the user. In this case, the processor 120 may estimate the user's SBP or DBP based on a reference MAP value at a calibration time, a reference pulse pressure value at a calibration time, and the reference SBP value and the reference DBP value at a calibration time, but is not limited thereto.

In another example, the processor 120 may estimate the user's SBP and DBP based on a variation in the estimated MAP compared to the reference MAP at the calibration time, and a variation in the estimated pulse pressure compared to the reference pulse pressure value at the calibration time.

In yet another example, the processor 120 may estimate a user's blood pressure based on a variation in feature value obtained at the time of blood pressure estimation, compared to the reference feature value obtained at the calibration time.

For example, the processor 120 may estimate the user's SBP or DBP based on the variation in the pulse pressure value obtained at the time of blood pressure estimation compared to the reference pulse pressure feature value obtained at the calibration time. For example, the processor 120 may estimate the user's SBP or DBP based on the variation in the obtained pulse pressure feature value compared to the user's reference pulse pressure feature value, the variation in the CO feature value obtained at the time of blood pressure estimation compared to the reference CO feature value obtained at the calibration time, a variation in the TPR feature value obtained at the time of blood pressure estimation compared to the reference TPR feature value obtained at the calibration time, and the reference SBP value or the reference DBP value which are obtained at the calibration time.

Figure 2:
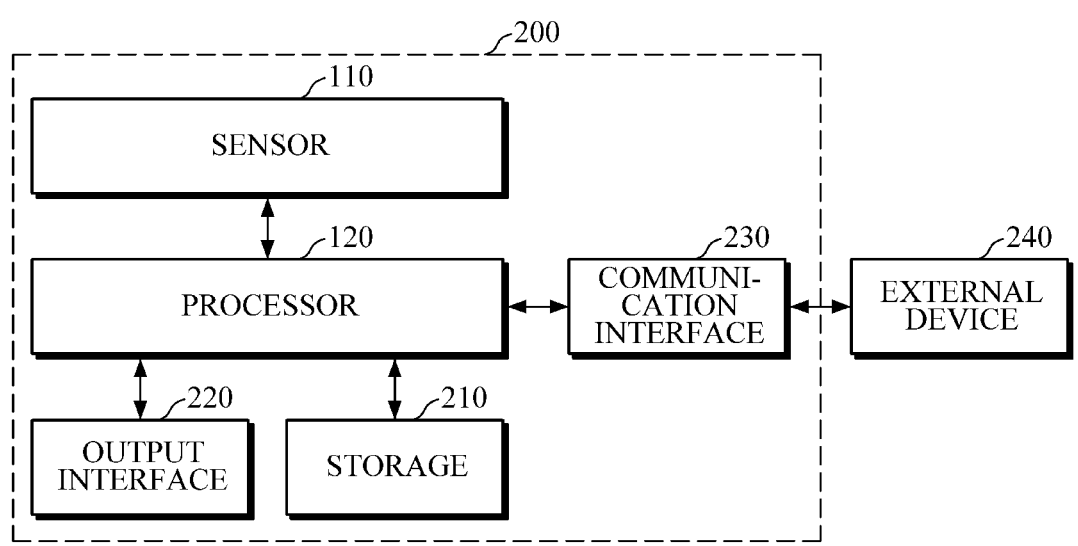
FIG. 2 is a block diagram illustrating an apparatus for estimating blood pressure according to another example embodiment.

FIG. 2 is a block diagram illustrating an apparatus for estimating blood pressure according to another example embodiment of the disclosure.

Referring to FIG. 2, an apparatus 200 for estimating blood pressure may include the sensor 110, the processor 120, a communication interface 230, an output interface 220, and a storage 210.

As described above, the sensor 110 may measure a PPG signal from an object. In this embodiment, the sensor 110 may be omitted, as will be described below.

The storage 210 may store a variety of reference information related to estimating pulse pressure and/or blood pressure, information such as the obtained PPG signal, pulse pressure and/or the estimated blood pressure value, and the like. In this case, the reference information may include user information, such as a user's age, gender, occupation, current health condition, etc., and information on a correlation between the PPG signal and the pulse pressure, and the like, but is not limited thereto. In this case, the storage 210 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The output interface 220 may output the PPG signal, measured by the sensor 110, and processing results of the processor 120, and may provide the information to the user. The output interface 220 may provide the information to the user by various visual and/or non-visual methods using a display module, a speaker, a haptic device, and the like which are mounted in the apparatus 200 for estimating blood pressure.

For example, the output interface 220 may output a waveform of the PPG signal and/or a waveform of the second-order derivative signal in a graph form. Further, the output interface 220 may display markers indicating pairs of local maximum points and local minimum points, the position of dicrotic notch, the obtained pulse pressure feature value and/or blood pressure feature value, the pulse pressure feature value and/or blood pressure feature value obtained at the calibration time, the reference pulse pressure, the reference blood pressure, and the like. Further, the output interface 220 may visually display the estimated blood pressure value, and may provide the value for a user by using various visual methods, such as by changing color, line thickness, font, etc., based on whether the estimated blood pressure value falls within or outside a normal range. In addition, the output interface 220 may provide vibration or tactile feedback based on whether the estimated blood pressure value is abnormal, so that the user may easily recognize the abnormal blood pressure value. Alternatively, upon comparing the estimated blood pressure value with a previous estimation history, if the estimated blood pressure value is abnormal, the output interface 220 may provide a warning message, an alarm signal, etc., as well as information on a user's action such as food information that the user should be careful about, relevant hospital information, and the like.

The communication interface 230 may be connected to an external device 240 using communication techniques under the control of the processor 120, and may receive a PPG signal from the external device 240. In this case, the external device 240 may include various devices, such as a smartphone, a tablet PC, a wearable device, a cuff type blood pressure measuring device, etc., capable of directly measuring the PPG signal or managing the measured PPG signal, without specific limitation.

Examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, and mobile communication. However, this is merely exemplary and is not intended to be limiting.

In the case where both the sensor 110 and the communication interface 230 are mounted in the apparatus 200 for estimating blood pressure, the processor 120 may obtain a PPG signal by selectively controlling the sensor 110 and the communication interface 230. The sensor 110 may be omitted depending on the characteristics of the apparatus 200.

Figure 3A:
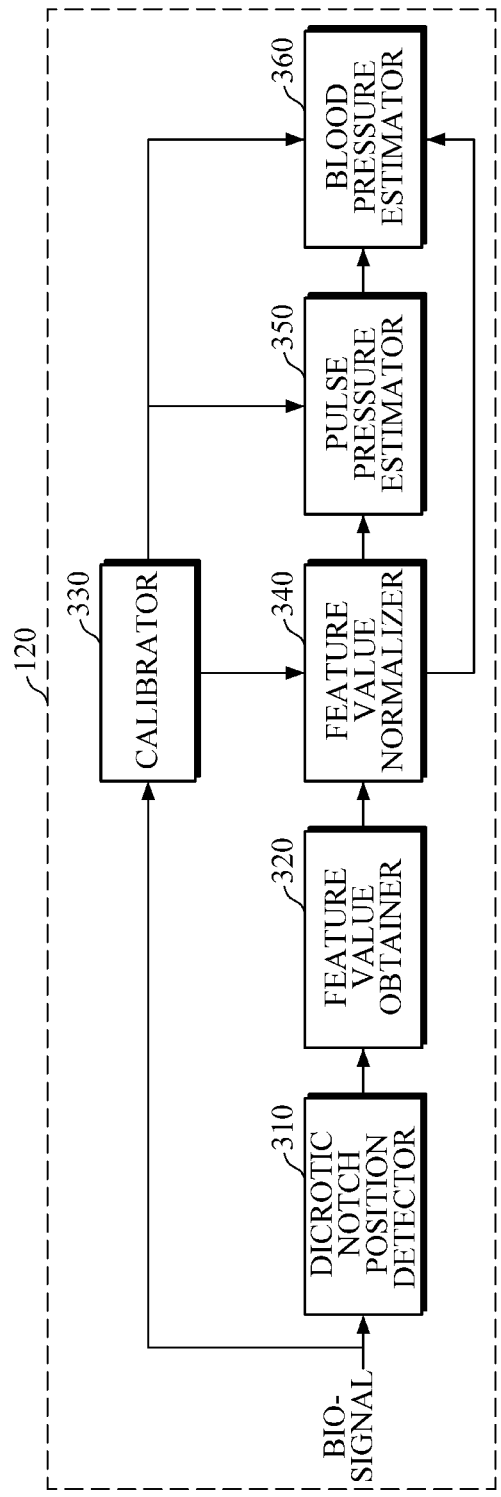
FIG. 3A is a block diagram illustrating a configuration of a processor according to an example embodiment.
Figure 3B:
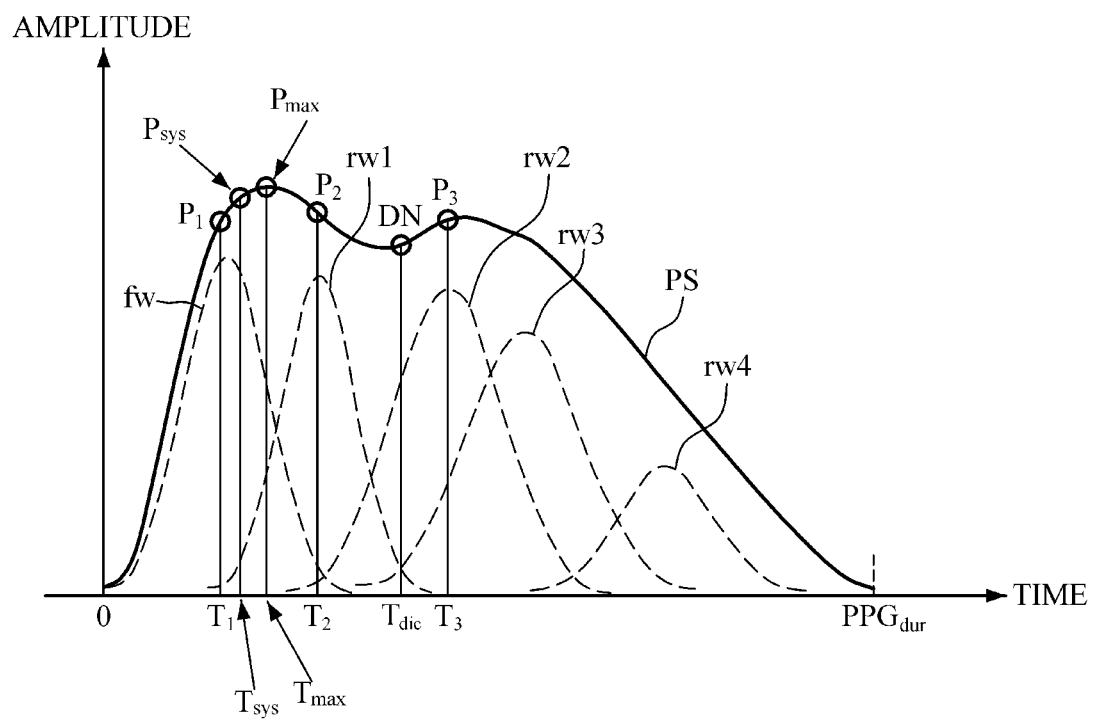
FIG. 3B is a diagram illustrating an example of a photoplethysmogram (PPG) signal acquired from an object.
Figure 3C:
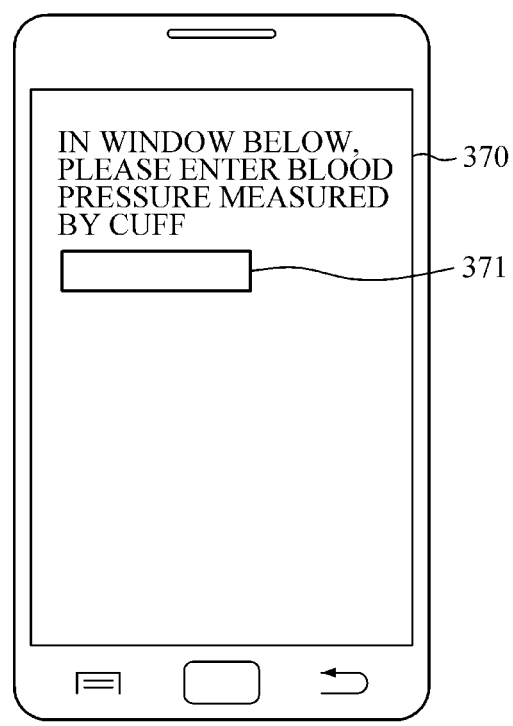
FIG. 3C is a diagram illustrating an example of a user interface for guiding a user to input a blood pressure value measured by an external device, and for showing an input position of the blood pressure value.
Figure 4A:
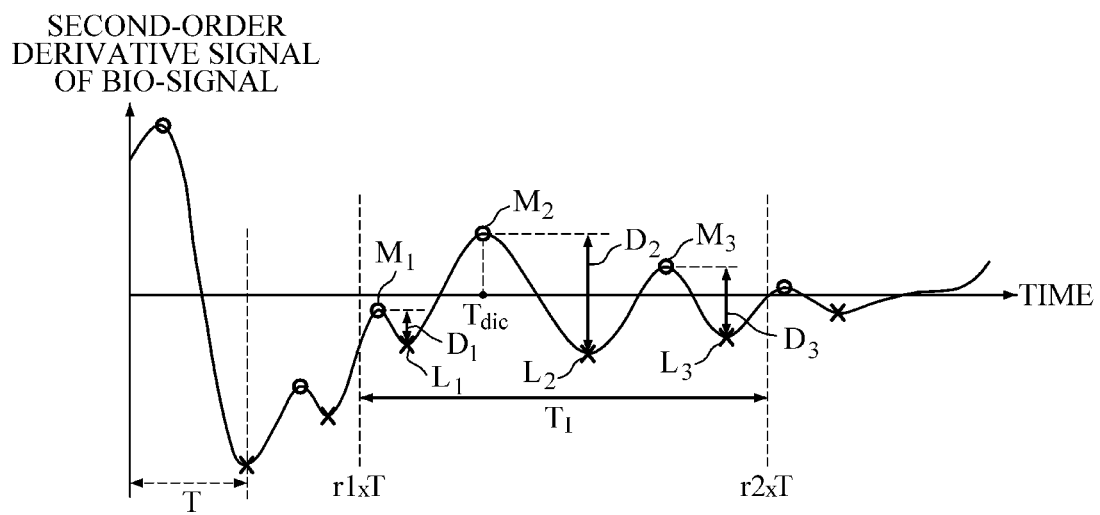
FIG. 4A is a diagram explaining an example of detecting a position of dicrotic notch.
Figure 4B:
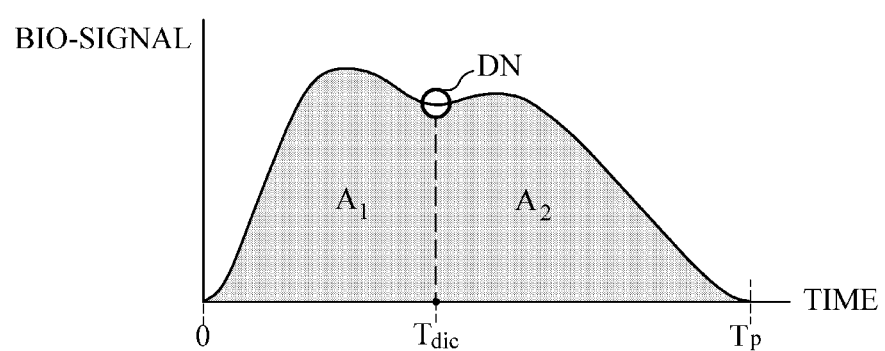
FIGS. 4B to 4D are diagrams explaining an example of obtaining a pulse pressure feature value based on a first value and a second value in two sections which are divided based on the dicrotic notch.
Figure 4C:
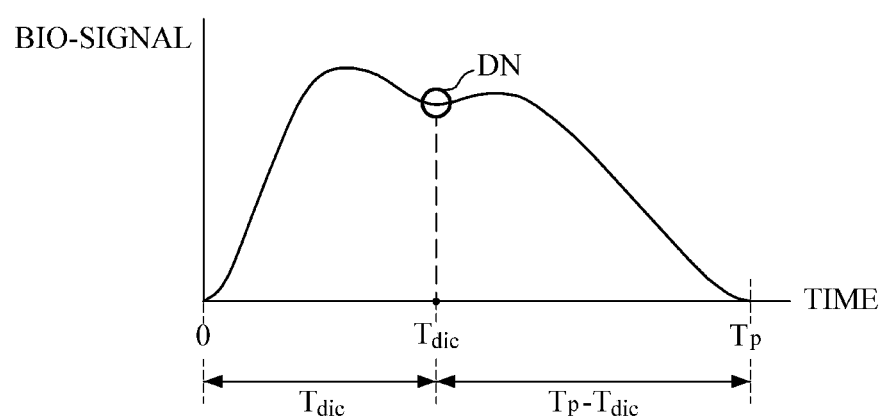
Figure 4D:
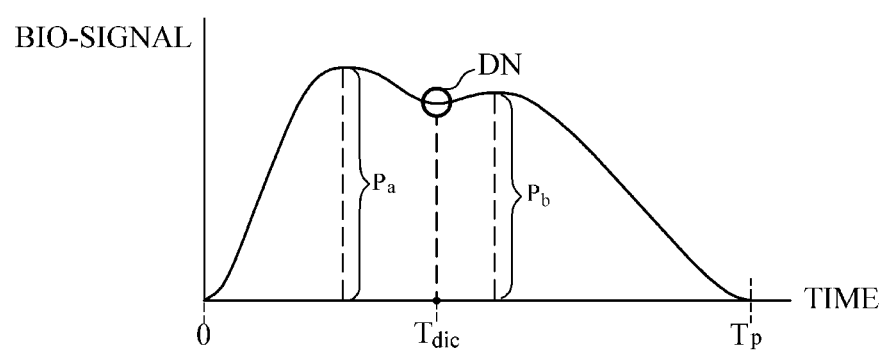

FIG. 3A is a block diagram illustrating a configuration of a processor according to an example embodiment. FIG. 3B is a diagram illustrating an example of a PPG signal obtained from an object. FIG. 3C is a diagram illustrating an example of a user interface for guiding a user to input a blood pressure value measured by an external device, and for showing an input position of the blood pressure value. FIG. 4A is a diagram explaining an example of detecting a position of dicrotic notch. FIGS. 4B, 4C, and 4D are diagrams explaining an example of obtaining a pulse pressure feature value based on a first value and a second value in two sections of a PPG signal which are divided based on the dicrotic notch.

Referring to FIG. 3A, the processor 120 may include a dicrotic notch position detector 310, a feature value obtainer 320, a calibrator 330, a feature value normalizer 340, a pulse pressure estimator 350, and a blood pressure estimator 360.

Upon receiving a PPG signal from the sensor 110, the dicrotic notch position detector 310 may obtain a second order derivative signal of the PPG signal. Further, the dicrotic notch position detector 310 may set a predetermined time range to detect a dicrotic notch position, and may detect the dicrotic notch position within the predetermined time range of the second-order derivative signal. For example, the dicrotic notch position detector 310 may determine pairs of local maximum points and local minimum points in the time range of the second-order derivative signal of the PPG signal, may calculate a difference between an amplitude at the local maximum point and an amplitude at the local minimum point for the respective determined pairs of local maximum points and local minimum points, and may detect the dicrotic notch position based on the difference.

Referring to FIG. 4A, an example of a second-order derivative signal of one PPG signal waveform is illustrated, in which T denotes a time up to a first local minimum point of the second-order derivative signal, r1 and r2 denote constants for setting a time range $T_1$ to detect the dicrotic notch position, and $T_{dic}$ denotes the dicrotic notch position.

For example, the dicrotic notch position detector 310 may determine the time T up to the first local minimum point of the second-order derivative signal as a reference time, as illustrated herein. Further, the time range $T_1$ is defined by defining a value (r1×T), obtained by multiplying the determined reference time T by the first constant r1, as a start point of the time range $T_1$, and defining a value (r2×T), obtained by multiplying the determined reference time T by the second constant r2, as an end point of the time range $T_1$. For example, the time range $T_1$ to detect a dicrotic notch position may be determined to be a range of 2T to 5T, but is not limited thereto.

Upon setting the time range $T_1$, the dicrotic notch position detector 310 may determine local maximum points in the time range $T_1$, and local minimum points appearing immediately after the local maximum points, as pairs $\{(M_1, L_1), (M_2, L_2), \text{ and } (M_3, L_3)\}$ of the local maximum points and the local minimum points. The dicrotic notch position detector 310 may calculate amplitude differences $D_1$, $D_2$, and $D_3$ between the local maximum points and the local minimum points for the respective determined pairs $\{(M_1, L_1), (M_2, L_2), \text{ and } (M_3, L_3)\}$ of the local maximum points and the local minimum points, and may detect a time point $T_{dic}$ of the local maximum point $M_2$ of the pair, having the largest amplitude difference $D_2$, as the dicrotic notch position.

In an ideal second-order derivative signal including no noise, a position of a third local maximum point may be generally detected as the dicrotic notch position, but in an actual environment, the PPG signal has various non-ideal waveforms due to noise, unstable body contact state, or unusual blood vessel structure characteristics, and the like. Accordingly, in an example embodiment, in order to remove such noise, the time point of the local maximum point of the pair, having the largest amplitude difference, is detected as the dicrotic notch position, thereby improving accuracy in estimating pulse pressure.

In addition, if a number of the pairs of the local maximum points and the local minimum points in the second-order derivative signal of the PPG signal is less than a predetermined number (e.g., three), or if a maximum value of the amplitude differences between the local maximum points and the local minimum points of the pairs of the local maximum points and the local minimum points is less than or equal to a threshold value, the dicrotic notch position detector 310 may indicate that a user needs to remeasure the PPG signal.

Referring back to FIG. 3A, the feature value obtainer 320 may obtain at least one of the pulse pressure feature value, the MAP feature value, the cardiac output feature value, and the total peripheral resistance feature value. In this case, the feature value obtainer 320 may obtain a reference feature value at the calibration time and/or the feature value at the time of blood pressure estimation. However, the reference feature value at the calibration time may also be obtained by the calibrator 330 which will be described later.

For example, when the PPG signal is divided into both sections based on the dicrotic notch position, the feature value obtainer 320 may obtain the first value and the second value from the both sections of the PPG signal, and may obtain the pulse pressure feature values based on the first value and the second value.

For example, referring to FIG. 4B, the feature value obtainer 320 may obtain, as the first value and the second value, areas $A_1$ and $A_2$ of the both sections of the PPG signal divided based on the position $T_{dic}$ of the dicrotic notch DN detected by the dicrotic notch position detector 310. For example, the feature value obtainer 320 may determine, as the first value, the area $A_1$ from the start point 0 to the dicrotic notch position $T_{dic}$ of the PPG signal in one period $T_P$, and may determine, as the second value, the area $A_2$ from the dicrotic notch position $T_{dic}$ to the end point $T_P$ of the PPG signal in one period $T_P$.

Further, the feature value obtainer 320 may obtain the pulse pressure feature value feat_PP based on the obtained first value $A_1$ and second value $A_2$. For example, the feature value obtainer 320 may obtain a ratio between the first value $A_1$ and the second value $A_2$ as the pulse pressure feature value feat_PP, which is represented in the following Equation 1.

$feat\_PP=A_1/A_2$ [Equation 1]

In another example, referring to FIG. 4C, the feature value obtainer 320 may obtain, as the first value and the second value, measurement times $T_{dic}$ and $T_p$-$T_{dic}$ in the respective both sections of the PPG signal divided based on the position $T_{dic}$ of the dicrotic notch DN detected by the dicrotic notch position detector 310. For example, the feature value obtainer 320 may determine, as the first value, the time $T_{dic}$ from the start point 0 to the dicrotic notch position $T_{dic}$ of the PPG signal in one period $T_p$, and may determine, as the second value, the time $T_p$-$T_{dic}$ from the dicrotic notch position $T_{dic}$ to the end point $T_p$.

Further, the feature value obtainer 320 may obtain the pulse pressure feature value feat_PP based on the obtained first value $T_{dic}$ and second value $T_p$-$T_{dic}$. For example, the feature value obtainer 320 may obtain a ratio between the first value $T_{dic}$ and second value $T_p$-$T_{dic}$ as the pulse pressure feature value feat_PP, which is represented by the following Equation 2.

$feat\_PP=T_{dic}/(T_p-T_{dic})$ [Equation 2]

In yet another example, referring to FIG. 4D, the feature value obtainer 320 may divide the PPG signal into two sections based on the position $T_{dic}$ of the dicrotic notch DN detected by the dicrotic notch position detector 310, and may obtain maximum amplitudes $P_a$ and $P_b$ of the PPG signal in the respective sections as the first value and the second value. For example, the feature value obtainer 320 may determine, as the first value, the maximum amplitude $P_a$ between the start point 0 and the dicrotic notch position $T_{dic}$ of the PPG signal in one period $T_p$, and may determine, as the second value, the maximum amplitude $P_b$ between the dicrotic notch position $T_{dic}$ and the end point $T_p$.

Further, the feature value obtainer 320 may obtain the pulse pressure feature value feat_PP based on the obtained first value $P_a$ and second value $P_b$. For example, the feature value obtainer 320 may obtain a ratio between the first value $P_a$ and second value $P_b$ as the pulse pressure feature value feat_PP, which is represented by the following Equation 3. However, the feature value obtainer 320 is not limited thereto, and a method of obtaining the pulse pressure feature value feat_PP based on the first value $P_a$ and second value $P_b$ may be modified variously.

$feat\_PP=P_a/P_b$ [Equation 3]

The feature value obtainer 320 may obtain an MAP feature value based on the measured PPG signal. For example, the feature value obtainer 320 may obtain a cardiac output feature value and a total peripheral resistance feature value from the PPG signal, and may obtain the MAP feature value feat_MAP_current by a linear or non-linear combination of the obtained cardiac output feature value and the total peripheral resistance feature value.

The feature value obtainer 320 may extract a characteristic point from the PPG signal, and may obtain the cardiac output feature value and/or the total peripheral resistance feature value based on the extracted characteristic point.

In this case, the characteristic point may include one or more a shape of a PPG signal waveform, the time and amplitude at a maximum point of the PPG signal, the time and amplitude at a minimum point of the PPG signal, the area of the PPG signal; a duration of the PPG signal, amplitude and time information of a constituent pulse waveform of the PPG signal, and an internally dividing point between two or more characteristic points, but the characteristic point is not limited thereto. Here, the PPG signal may be the aforementioned representative pulse of the PPG signal.

FIG. 3B is a diagram illustrating an example of a PPG signal acquired from an object. Referring to FIG. 3B, the following description will be given of an example in which the feature value obtainer 320 extracts characteristic points from the PPG signal.

The PPG signal may be formed by a summation of a propagation wave propagating from the heart to peripheral parts of the body and reflection waves returning from the peripheral parts. In FIG. 3B, a waveform of the PPG signal acquired from the object is a summation of five constituent pulses, for example, a propagation wave fw and reflection waves rw1, rw2, rw3, and rw4. The feature value obtainer 320 may extract characteristic points by analyzing the constituent pulse waveforms fw, rw1, rw2, rw3, and rw4.

For example, the feature value obtainer 320 may extract, as characteristic points, times $T_1$, $T_2$, and $T_3$ or amplitudes $P_1$, $P_2$, and $P_3$ at maximum points of the first to third constituent pulse waveforms fw, rw1, and rw2. In this case, by taking the second order derivative of the PPG signal PS and by using the second-order derivative signal, the feature value obtainer 320 may extract the times $T_1$, $T_2$, and $T_3$ at the maximum points of the constituent pulse waveforms fw, $rw_1$, and $rw_2$. For example, by detecting local minimum points from the second-order derivative signal, the feature value obtainer 320 may extract the times $T_1$, $T_2$, and $T_3$ respectively corresponding to the first, second, and third local minimum points, and may extract amplitudes $P_1$, $P_2$, and $P_3$ respectively corresponding to the times $T_1$, $T_2$, and $T_3$ from the PPG signal. Here, the local minimum point refers to a specific point, observed in a portion of the second-order derivative signal, at which the signal decreases and then increases again, that is, a downward convex point.

In another example, the feature value obtainer 320 may obtain, as characteristic points, a time $T_{max}$ and an amplitude $P_{max}$, at which an amplitude is maximum in one period (0 to $PPG_{dur}$) of the PPG signal PS, or in a predetermined interval of the one period (0 to $PPG_{dur}$) of the PPG signal PS. For example, the predetermined interval may refer to an interval from a start point of the PPG signal PS to the time point $T_{dic}$ at which the dicrotic notch (DN) occurs, which indicates a systolic phase of blood pressure.

In yet another example, the feature value obtainer 320 may obtain, as characteristic points, a duration $PPG_{dur}$ indicating one period of the PPG signal, or an area $PPG_{area}$ of the PPG signal. In this case, the area of the PPG signal may refer to a total area of the PPG signal, or an area of the PPG signal which corresponds to a predetermined percentage (e.g., 70%) of the entire duration $PPG_{dur}$ of the PPG signal.

In still another example, the feature value obtainer 320 may extract, as an additional characteristic point, an internally dividing point between the extracted two or more characteristic points. When the PPG signal has an unstable waveform due to an abnormal environment such as motion noise, sleep, etc., characteristic points may be extracted at wrong positions. The measurement of blood pressure may be supplemented by using the internally dividing point between the erroneously extracted characteristic points.

For example, upon extracting characteristic points ($T_1$, $P_1$) and ($T_{max}$, $P_{max}$), the feature value obtainer 320 may calculate an internally dividing point ($T_{sys}$, $P_{sys}$) between the extracted characteristic points ($T_1$, $P_1$) and ($T_{max}$, $P_{max}$). In this case, the feature value obtainer 320 may apply a weight to time values $T_1$ and $T_{max}$ of the two characteristic points ($T_1$, $P_1$) and ($T_{max}$, $P_{max}$), may calculate a time $T_{sys}$ of the internally dividing point by using the respective weighted time values, and may extract an amplitude $P_{sys}$ corresponding to the calculated time $T_{sys}$ of the internally dividing point. However, the internally dividing point is not limited thereto, and by analyzing the obtained PPG signal, the feature value obtainer 320 may further calculate an internally dividing point between the characteristic points ($T_1$, $P_1$) and ($T_2$, $P_2$) associated with the first and second constituent pulse waveforms fw and $rw_1$, and an internally dividing point between the characteristic points ($T_3$, $P_3$) and ($T_4$, $P_4$) associated with the third and fourth constituent pulse waveforms $rw_2$ and $rw_3$, and the like.

The feature value obtainer 320 may obtain the cardiac output feature value and/or the total peripheral resistance feature value based on the extracted characteristic points. In this case, the feature value obtainer 320 may obtain the cardiac output feature value and/or the total peripheral resistance feature value based on at least one of the plurality of characteristic points extracted by the feature value obtainer 320, and/or heart rate.

For example, the feature value obtainer 320 may obtain, as the cardiac output feature value and/or the total peripheral resistance feature value, time and amplitude at a point where the constituent pulse is maximum, a total measurement time of the PPG signal or a time up to the dicrotic notch position $T_{dic}$, a total area or a partial area of the PPG signal, either one of the time at which amplitude is maximum in a predetermined interval of the PPG signal, or the amplitude, or a reciprocal number thereof, the heart rate, and the like, which are the extracted characteristic points.

In another example, the feature value obtainer 320 may obtain the cardiac output feature value and/or the total peripheral resistance feature value based on a statistical value obtained by combining at least two or more of the extracted plurality of characteristic points and the heart rate. For example, the feature value obtainer 320 may obtain, as the cardiac output feature value and/or the total peripheral resistance feature value, a value obtained by dividing a maximum amplitude of the constituent pulse by a maximum amplitude in the entire period of the PPG signal, a value obtained by dividing the maximum amplitude in the entire period of the PPG signal by the total area of the PPG signal, a value obtained by subtracting a time value at the internally dividing point from a time value corresponding to the maximum amplitude of the constituent pulse, or a reciprocal number thereof, a value obtained by subtracting the maximum amplitude of the constituent pulse from the maximum amplitude in the entire period of the PPG signal, or a reciprocal number thereof, a statistical value of the maximum amplitude in the entire period of the PPG signal and the heart rate, and the like.

The following Table 1 shows candidates of the cardiac output (CO) feature value and/or the total peripheral resistance (TPR) feature value with respect to FIG. 3B described above, but the embodiment is not limited thereto.

TABLE 1

| No. | Candidates of CO feature value and/or TPR feature value |
|---|---|
| 1 | Heart rate (HR) |
| 2 | $PPG_{area}$ |
| 3 | $P_3/P_{max}$ |
| 4 | $P_3/P_{sys}$ |
| 5 | $P_{max}/PPG_{area}$ |
| 6 | $1/PPG_{dur}$ |
| 7 | $1/(T_3 - T_1)$ |
| 8 | $1/(T_3 - T_{sys})$ |
| 9 | $1/(T_3 - T_{max})$ |
| 10 | $1/(T_2 - T_1)$ |
| 11 | $P_2/P_1$ |
| 12 | $P_3/P_{max}$ |
| 13 | $P_3/P_1$ |

The pulse pressure feature value, the MAP feature value, the cardiac output feature value, and the total peripheral resistance feature value, which are obtained by the feature value obtainer 320, may be transmitted to the feature value normalizer 340.

In the case where a user measures blood pressure by using the apparatuses 100 and 200 for estimating blood pressure, calibration needs to be performed first. The calibrator 330 may perform calibration based on a predetermined period, pulse pressure, and/or analysis of a blood pressure estimation result, or according to a user's request.

For example, the calibrator 330 may perform calibration at an initial time point of use, and at predetermined intervals from the initial time point of use. For example, when a user requests to estimate an initial blood pressure value by using the apparatus 100, the calibrator 330 may check whether there is reference information to be used for estimating blood pressure by referring to the storage, and if there is no reference information, the calibrator 330 may perform calibration.

In another example, the calibrator 330 may analyze the pulse pressure and/or the blood pressure estimation result and may determine whether to perform calibration based on the analysis. For example, once blood pressure estimation is complete, the calibrator 330 may determine accuracy of the estimated blood pressure to determine whether to perform calibration. For example, a normal range of the estimated blood pressure value may be pre-defined, and if the estimated blood pressure value falls outside the normal range, if a number of times the estimated blood pressure value falls outside the normal range exceeds a threshold value, if a number of times the estimated blood pressure value continuously fails to satisfy the normal range is greater than or equal to a predetermined threshold value, and if a number of times the estimated blood pressure value fails to satisfy the normal range during a predetermined period is greater than or equal to a predetermined threshold value, etc., the calibrator 330 may determine that calibration is needed.

Upon determining to perform calibration, the calibrator 330 may control the sensor 110 to acquire a PPG signal for calibration. The calibrator 330 may guide a user to place an object on the sensor 110, or may guide the user on the connection to an external device through the communication interface 210, or may guide the user to measure reference blood pressure using the external device.

In this case, by controlling, for example, the communication interface 230 of FIG. 2, the calibrator 330 may receive reference information at the calibration time from the external device, e.g., reference blood pressure information, such as cuff systolic blood pressure, cuff diastolic blood pressure, etc., obtained from a cuff sphygmomanometer.

Alternatively, the calibrator 330 may display a user interface 370 illustrated in FIG. 3C on a display, and may guide the user to input a systolic blood pressure value and a diastolic blood pressure value, measured using the external device, through the user interface 370. Referring to FIG. 3C, the user interface 370 of the apparatus for estimating blood pressure may include a graphic object 371, which may be selected (e.g., touched) by the user to enter the blood pressure values measured using the external device.

Once the sensor 110 acquires the PPG signal for calibration, the calibrator 330 may obtain reference information to be used for estimating blood pressure by using the PPG signal for calibration, and may store the obtained reference information in the storage for use in blood pressure estimation at a later time.

For example, the calibrator 330 may obtain a reference pulse pressure feature value feat_PP_cal at the calibration time, a reference MAP feature value feat_MAP_cal, a reference CO feature value, and a reference TPR feature value. The reference MAP feature value feat_MAP_cal may be obtained by a linear or non-linear combination of the reference CO feature value and the reference TPR feature value which are obtained at the calibration time. The reference CO feature value and the reference TPR feature value may be obtained based on the characteristic points extracted from the PPG signal measured at the calibration time. In this case, the calibrator 330 may obtain the CO feature value and/or the TPR feature value based on at least one or more of the extracted characteristic points, and/or the heart rate. A detailed description thereof will be omitted.

Further, the calibrator 330 may obtain reference pulse pressure PP_cal at the calibration time, by using reference systolic blood pressure SBP_cal and reference diastolic blood pressure DBP_cal which are received through the communication interface 230 or input through the user interface 370. The reference pulse pressure may be obtained by subtracting (PP_cal=SBP_cal−DBP_cal) the reference diastolic blood pressure from the reference systolic blood pressure.

The calibrator 330 may obtain the reference MAP value MAP_cal at the calibration time by using the reference diastolic blood pressure DBP_cal and the reference pulse pressure PP_cal at the calibration time. The reference MAP value MAP_cal may be obtained by using the following Equation 4, but is not limited thereto.

$$MAP\_cal = \alpha(PP\_cal) + DBP\_cal \qquad \text{[Equation 4]}$$

Herein, PP_cal is the reference pulse pressure at the calibration time; DBB_cal is the reference diastolic blood pressure at the calibration time; and α may denote a fixed constant or a variable that changes according to the heart rate, in which when α is a variable that changes according to the heart rate, α may increase as the heart rate increases.

The feature value normalizer 340 may calculate variations in the respective feature values by normalizing the obtained pulse pressure feature value, MAP feature value, CO feature value, and/or TPR feature value.

For example, by using the pulse pressure feature value feat_PP_cal at the calibration time, the feature value normalizer 340 may perform normalization to show a ratio by which a current pulse pressure feature value feat_PP_current increases or decreases from the pulse pressure feature value feat_PP_cal at the initial calibration time. A value obtained as a result of the normalization of the pulse pressure feature value, i.e., a variation in pulse pressure feature value, may indicate Δfeat_PP in the following Equations 7, 13, and 14. Further, the variation Δfeat_PP in pulse pressure feature value may be used for calculating a pulse pressure variation ΔPP_est at the time of blood pressure estimation compared to the reference pulse pressure at the calibration time in Equations 11 and 12.

In another example, by using the MAP feature value feat_MAP_cal at the calibration time, the feature value normalizer 340 may perform normalization to show a ratio by which a current MAP feature value feat_MAP_current increases or decreases from the MAP feature value feat_MAP_cal at the initial calibration time. A value obtained as a result of the normalization of the MAP feature value, i.e., a variation in the MAP feature value, may indicate Δfeat_MAP in the following Equation 8. Further, the variation Δfeat_MAP in the MAP feature value may be used for calculating a MAP variation ΔMAP_est at the time of blood pressure estimation compared to the reference MAP at the calibration time in Equations 11 and 12.

In yet another example, by using the above method, the feature value normalizer 340 may calculate a variation in CO feature value feat_CO and/or a variation in TPR feature value feat_TPR.

$$\Delta feat\_CO = \left( \frac{feat\_CO\_current}{feat\_CO\_cal} - 1 \right) \qquad \text{[Equation 5]}$$

$$\Delta feat\_TPR = \left( \frac{feat\_TPR\_current}{feat\_TPR\_cal} - 1 \right) \qquad \text{[Equation 6]}$$

In this case, Δfeat_CO denotes the variation in cardiac output feature value; feat_CO_current denotes the cardiac output feature value obtained at the time of blood pressure measurement; feat_CO_cal denotes the reference cardiac output feature value obtained at the calibration time; Δfeat_TRP denotes the variation in total peripheral resistance feature value; feat_TPR_current denotes the total peripheral resistance feature value obtained at the time of blood pressure measurement; and feat_TPR_cal denotes the reference total peripheral resistance feature value obtained at the calibration time.

The feature value normalizer 340 may transmit the variation in pulse pressure feature value to the pulse pressure estimator 370, or may transmit the variation in the MAP feature value, the variation in CO feature value, and the variation in TPR feature value to the blood pressure estimator 370.

The pulse pressure estimator 350 may estimate a user's pulse pressure by using the following Equation 7. That is, the pulse pressure estimator 350 may estimate pulse pressure based on the reference pulse pressure PP_cal obtained by the calibrator 330 and the variation in pulse pressure feature value transmitted from the feature value normalizer 340.

$$PP\_est = SF\_PP \times \Delta feat\_PP + PP\_cal \quad \text{[Equation 7]}$$

$$\Delta feat\_PP = \left(\frac{feat\_PP\_current}{feat\_PP\_cal} - 1\right)$$

Herein, PP_est denotes the pulse pressure to be estimated; Δfeat_PP denotes the variation in pulse pressure feature value transmitted from the feature value normalizer 330; PP_cal denotes the reference pulse pressure (=reference systolic blood pressure—reference diastolic blood pressure) obtained from the reference systolic blood pressure and the reference diastolic blood pressure which are measured at the calibration time; feat_PP_cal denotes the reference pulse pressure feature value extracted from the PPG signal measured at the calibration time; feat_PP_current denotes the pulse pressure feature value extracted from the current PPG signal; and SF_PP denotes a scale factor for estimating the variation in pulse pressure compared to the pressure at the calibration time, in which the scale factor SF_PP may be a constant in a range of 20 to 50, but is merely an exemplary value and is not limited thereto.

The blood pressure estimator 360 may estimate at least one of a user's MAP, SBP, and DBP.

The blood pressure estimator 360 may estimate the user's MAP by using an MAP estimation equation as represented by the following Equation 8.

$$MAP\_est = SF\_MAP \times \Delta feat\_MAP + MAP\_cal \quad \text{[Equation 8]}$$

$$\Delta feat\_MAP = \left(\frac{feat\_MAP\_current}{feat\_MAP\_cal} - 1\right)$$

Herein, MAP_est denotes the estimated MAP value to be obtained; Δfeat_MAP denotes the variation in the MAP feature value transmitted from the feature value normalizer 330; MAP_cal denotes the reference MAP value at the calibration time; feat_MAP_current denotes the MAP feature value obtained based on the PPG signal acquired at the blood pressure estimation time; feat_MAP_cal denotes the reference MAP feature value at the calibration time; and SF_MAP denotes the scale factor related to estimating MAP.

In this case, the MAP feature value feat_MAP_current at the time of MAP estimation may be a value obtained by an appropriate linear or non-linear combination of the obtained CO feature value and TPR feature value by the feature value obtainer 320, as described above. In this case, the CO feature value and/or the TPR feature value may be any one of the extracted characteristic points, the heart rate, and a statistical value obtained by a combination thereof. A detailed description thereof will be omitted. SF-MAP is the scale factor for estimating the MAP variation compared to MAP at the calibration time, and may be a constant within a predetermined range.

The blood pressure estimator 360 may estimate a user's SBP or DBP.

For example, the blood pressure estimator 360 may estimate the user's SBP or DBP based on the user's estimated MAP and pulse pressure.

An example of estimating the user's SBP or DBP based on the user's MAP and pulse pressure is represented in the following Equation 9 or 10, but is not limited thereto.

$$SBP\_est = MAP\_est + (1-k)PP\_est \quad \text{[Equation 9]}$$

$$DBP\_est = MAP\_est - k \times PP\_est \quad \text{[Equation 10]}$$

In Equation 9, SBP_est denotes the user's estimated SBP, and in Equation 10, DBP_est denotes the user's estimated DBP. Herein, MAP_est denotes the user's MAP estimated as described above, and PP_est denotes the user's pulse pressure estimated as described above. Further, k may be a prescribed constant or a function that increases in proportion to the increase of heart rate HR, but is not limited thereto.

In another example, the blood pressure estimator 360 may estimate the user's SBP or DBP based on the variation in the estimated MAP compared to the reference MAP value at the calibration time, the variation in the estimated pulse pressure compared to the reference pulse pressure value at the calibration time, and SBP or DBP at the calibration time.

An example thereof is represented in the following Equation 11 or 12, but is not limited thereto.

$$SBP\_est = \Delta MAP\_est + (1-k)\Delta PP\_est + SBP\_cal \quad \text{[Equation 11]}$$

$$DBP\_est = \Delta MAP\_est - k \times \Delta PP\_est + DBP\_cal \quad \text{[Equation 12]}$$

In Equation 11, SBP_est denotes the user's estimated SBP, and in Equation 12, DBP_est denotes the user's estimated DBP.

Herein, ΔPP_est denotes the variation in the estimated pulse pressure compared to the reference pulse pressure at the calibration time, i.e., (PP_est−PP_cal), in which PP_est denotes the user's pulse pressure estimated as described above, and PP_cal denotes a reference pulse pressure value at the calibration time, as described above. In this case, ΔPP_est may be obtained based on the variation in pulse pressure feature value represented in Equation 7, i.e., Δfeat_PP, without estimating the user's pulse pressure.

ΔMAP_est denotes the variation in the estimated MAP compared to the MAP at the calibration time, i.e., (MAP_est−MAP_cal), in which MAP_est denotes the user's MAP estimated as described above, and MAP_cal denotes the MAP value at the calibration time as described above. In this case, ΔMAP_est may be obtained based on the variation in the MAP feature value represented in Equation 8, i.e., Δfeat_MAP, without estimating the user's MAP.

Further, in this case, k may be a prescribed constant or a function that increases in proportion to the increase of heart rate HR, but is not limited thereto, and SBP_cal and DBP_cal denote SBP and DBP at the calibration time, respectively.

In yet another example, the blood pressure estimator 360 may estimate the user's SBP or DBP based on the variation in feature value at the time of blood pressure estimation compared to a reference feature value at the calibration time, and the reference blood pressure.

For example, the blood pressure estimator 360 may estimate the user's SBP or DBP by a linear combination of the variation in CO feature value, the variation in TPR feature value, the variation in pulse pressure, and the reference blood pressure. In this case, the reference blood pressure refers to the reference SBP or reference DBP.

An example of the linear combination may include a weighted sum, which is represented in Equations 13 and 14.

$$SBP\_est = a \times \Delta feat\_CO + b \times \Delta feat\_TPR + c \times \Delta feat\_PP + d \times SBP\_cal \quad \text{[Equation 13]}$$

In Equation 13, SBP_est denotes the SBP at the time of blood pressure measurement which is estimated by the blood pressure estimator 360; SBP_cal denotes the reference SBP obtained at the calibration time; Δfeat_CO denotes the variation in CO feature value; Δfeat_TPR denotes the variation in TPR feature value; and Δfeat_PP denotes the variation in pulse pressure feature value, in which a, b, c, and d are real numbers and may be different from each other, among which two or more thereof may be the same value. Further, at least one of a, b, c, and d may be 1 or zero.

$$DBP\_est = a \times \Delta feat\_CO + b \times \Delta feat\_TPR + c \times \Delta feat\_PP + d \times DBP\_cal \quad \text{[Equation 14]}$$

In Equation 14, DBP_est denotes the DBP at the time of blood pressure measurement which is estimated by the blood pressure estimator 360; DBP_cal denotes the reference DBP obtained at the calibration time; Δfeat_CO denotes the variation in CO feature value described above with reference to Equation 5; Δfeat_TPR denotes the variation in TPR feature value described above with reference to Equation 6; and Δfeat_PP denotes the variation in pulse pressure feature value described above with reference to Equation 7, in which a, b, c, and d are real numbers and are the same as those defined in Equation 14. However, the values are not limited thereto, and at least one of a, b, c, and d used in Equation 15 may be different from a, b, c, and d used in Equation 14. Further, Δfeat_CO, Δfeat_TPR, and Δfeat_PP in Equation 14 may be the same as or different from Δfeat_CO, Δfeat_TPR, and Δfeat_PP in Equation 13.

Figure 5:
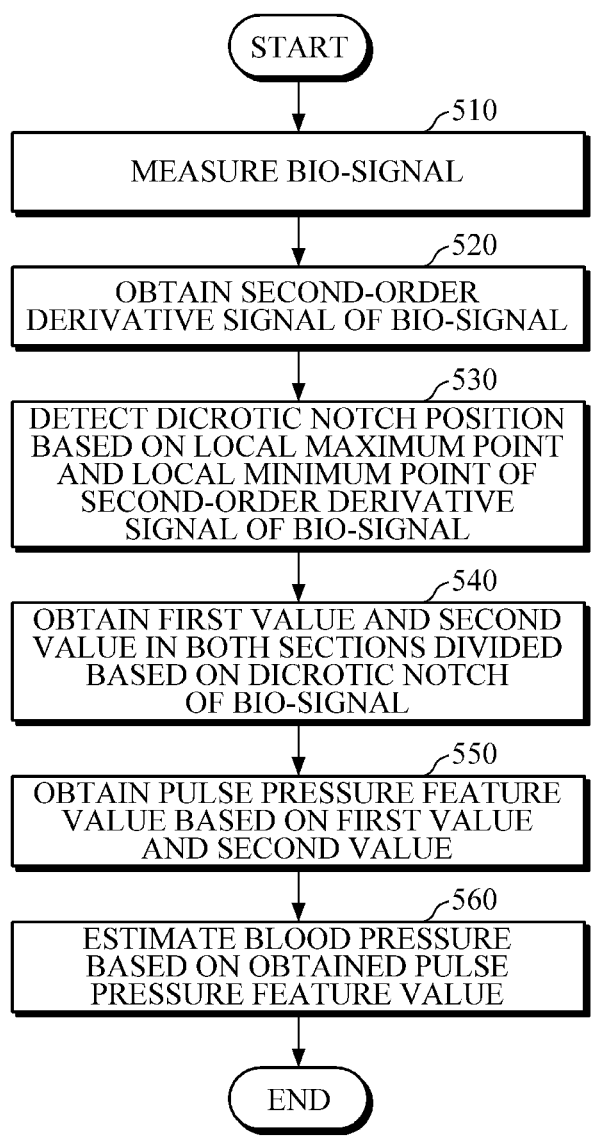
FIG. 5 is a flowchart illustrating a method of estimating blood pressure according to an example embodiment.

FIG. 5 is a flowchart illustrating a method of estimating blood pressure according to an example embodiment. The method of FIG. 5 is an example of a method of estimating blood pressure performed by the apparatus for estimating blood pressure of FIG. 1 or FIG. 2, which is described above in detail, and thus will be briefly described below.

First, upon receiving a request for estimating blood pressure, the apparatus for estimating blood pressure may measure a PPG signal in 510. The apparatuses 100 and 200 for estimating blood pressure may provide an interface for various interactions with a user. The user may request to estimate pulse pressure through the interface provided by the apparatus for estimating blood pressure. Alternatively, the apparatus for estimating blood pressure may receive a request for estimating blood pressure from an external device. In this case, the request for estimating blood pressure, which is received from the external device, may include a request for providing a blood pressure estimation result. In the case where the external device includes an algorithm for estimating blood pressure, the request for estimating blood pressure may include a request for providing obtained feature values. Examples of the external device may include a smartphone, a tablet PC, a laptop computer, a wearable device, and the like. The apparatus for estimating blood pressure may control the sensor to measure the PPG signal, including a pulse wave signal, from the object.

Subsequently, the apparatus for estimating blood pressure may obtain a second-order derivative signal of the PPG signal in 520, and then may detect a dicrotic notch position based on a local maximum point and a local minimum point of the second-order derivative signal of the PPG signal in 530. For example, the apparatus for estimating blood pressure may determine pairs of the local maximum points and local minimum points, may calculate a difference between a second-order derivative value at the local maximum point and a second-order derivative value at the local minimum point in the pairs of the local maximum points and local minimum points, and may detect the dicrotic notch position based on the difference. In an example, the apparatus for estimating blood pressure may detect a local maximum point of a pair, having the largest difference between the second-order derivative value at the local maximum point and the second-order derivative value at the local minimum point, as the dicrotic notch position.

Next, the apparatus for estimating blood pressure may obtain the first value and the second value in both sections divided based on the dicrotic notch of the PPG signal in 540. For example, the first value and the second value may include any one of an area of the PPG signal in each corresponding section, a measurement time of the respective sections, amplitude data of the PPG signal in the respective sections, and an intensity of an nth (n being an integer equal to or greater than 1) order derivative signal of the PPG signal in the respective sections, but the values are not limited thereto.

Then, the apparatus for estimating blood pressure may obtain a pulse pressure feature value based on the first value and the second value in 550. In this case, the pulse pressure feature value may include a ratio between the first value and the second value, but is not limited thereto.

Subsequently, the apparatus for estimating blood pressure may estimate blood pressure based on the pulse pressure feature value in 560.

For example, by estimating pulse pressure based on the pulse pressure feature value by using a pre-defined pulse pressure estimation model and by estimating MAP based on the MAP feature value, the apparatus for estimating blood pressure may estimate SBP or DBP based on the estimated pulse pressure and MAP.

In another example, the apparatus for estimating blood pressure may estimate SBP or DBP based on a variation in the estimated MAP compared to a reference MAP value at the calibration time, and a variation in the estimated pulse pressure compared to a reference pulse pressure value at the calibration time.

In yet another example, the apparatus for estimating blood pressure may estimate SBP or DBP based on a variation in the obtained pulse pressure feature value compared to a reference pulse pressure feature value. In this case, the apparatus for estimating blood pressure may estimate SBP or DBP based further on a variation in the obtained CO feature value compared to a reference CO feature value, a variation in the obtained TPR feature value compared to a reference TPR feature value, and a reference SBP value or a reference DBP value. A detailed description thereof will be omitted.

Figure 6:
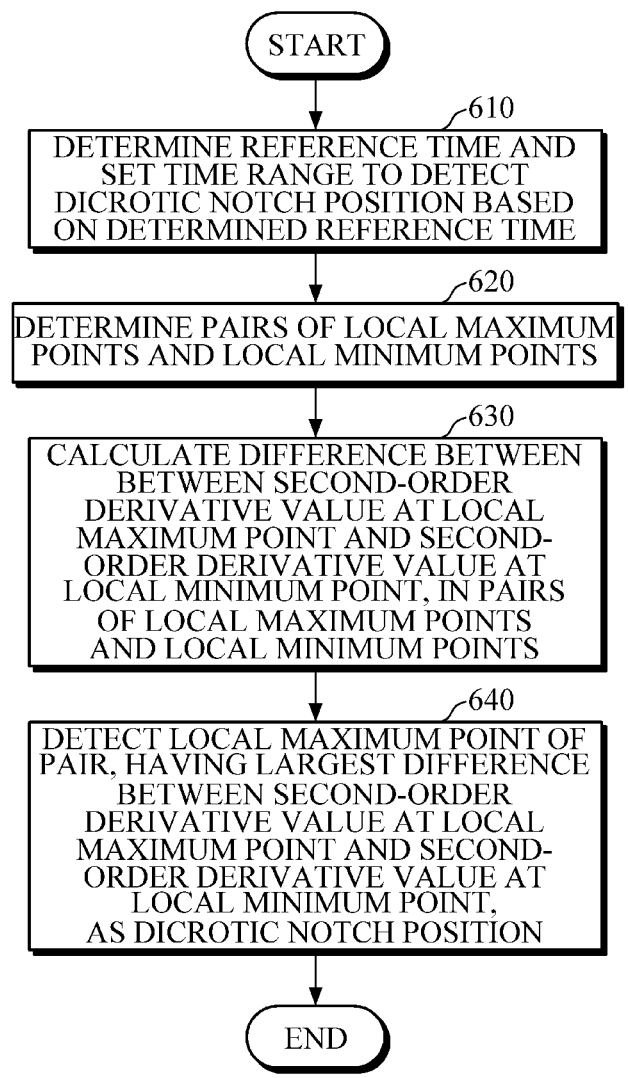
FIG. 6 is a diagram illustrating an example of detecting a dicrotic notch position in 530 of FIG. 5.

FIG. 6 is a diagram illustrating an example of detecting a dicrotic notch position in 530 of FIG. 5.

First, in 610, the apparatus for estimating blood pressure may determine, as a reference time, at least any one of a period of the PPG signal and a time up to a first local minimum point of the second-order derivative signal of the PPG signal, and may set a time range to detect the dicrotic notch position based on the determined reference time. In this case, the time range may be set by defining a value, obtained by multiplying the reference time by a first constant, as a start point of the time range and by defining a value, obtained by multiplying the reference time by a second constant, as an end point of the time range, but is not limited thereto.

Then, the apparatus for estimating blood pressure may determine pairs of local maximum points and local minimum points in the second-order derivative signal of the PPG signal in 620. In this case, the apparatus for estimating blood pressure may determine a first detected local maximum point and a first detected local minimum point as a pair, and may determine local maximum points and local minimum points, which are detected thereafter, as other pairs in time sequential order.

Here, the apparatus for estimating blood pressure may determine whether a number of the determined pairs is less than a predetermined number (e.g., three), and if the number of the determines pairs is less than the predetermined number, the apparatus for estimating blood pressure may request a user to remeasure the PPG signal.

Then, the apparatus for estimating blood pressure may calculate a difference between a second-order derivative value at the local maximum point and a second-order derivative value at the local minimum point, in the pairs of the local maximum points and the local minimum points in 630.

Subsequently, the apparatus for estimating blood pressure may detect a local maximum point of a pair, having the largest difference between the second-order derivative value at the local maximum point and the second-order derivative value at the local minimum point, as the dicrotic notch position in 640. In this case, in the pair having the largest difference between the second-order derivative value at the local maximum point and the second-order derivative value at the local minimum point, if the difference therebetween is less than or equal to a threshold value, the apparatus for estimating blood pressure may request a user to remeasure the PPG signal.

Figure 7:
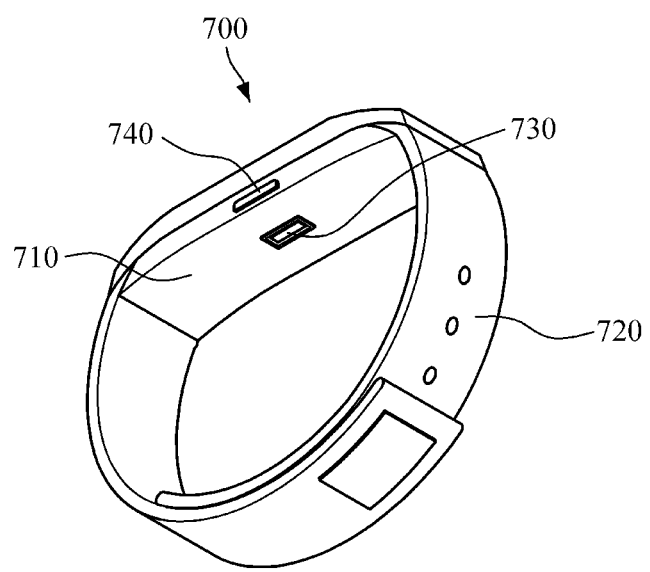
FIG. 7 is a diagram illustrating a wearable device according to an example embodiment.

FIG. 7 is a diagram illustrating a wearable device according to an example embodiment. Various embodiments of the aforementioned apparatuses 100 and 200 for estimating blood pressure may be mounted in a smart watch worn on a wrist, but the type of the wearable device is not limited thereto.

Referring to FIG. 7, a wearable device 700 includes a main body 710 and a strap 720.

The strap 720 may be made of a flexible material. The strap 720 may be connected to both ends of the main body 710, and may be wrapped around a user's wrist so that the main body 710 may be pressed against an upper portion of the wrist. In this case, air may be injected into the strap 720 or the strap 720 may be provided with an air bladder, so as to have elasticity according to a change in pressure applied to the wrist, and the change in pressure of the wrist may be transmitted to the main body 710.

A battery may be embedded in the main body 710 or the strap 720 to supply power to the wearable device 700. In addition, a sensor 730 may be mounted on a rear surface of the main body 710. The sensor 730 may include one or more light sources and a detector as described above.

For example, a processor may be mounted inside the main body 710, and may estimate pulse pressure and/or blood pressure by obtaining a second-order derivative signal of the PPG signal measured by the sensor 730. For example, the processor may detect a dicrotic notch position based on a local maximum point and a local minimum point of the second-order derivative signal of the PPG signal, may obtain a first value and a second value from both sections divided based on the dicrotic notch, may obtain a pulse pressure feature value based on the first value and the second value, and may estimate blood pressure based on the pulse pressure feature value.

The processor may be mounted inside the main body 710, and may estimate a user's blood pressure by obtaining a second-order derivative signal of the PPG signal measured by the sensor 730. For example, the processor may obtain the second-order derivative signal of the PPG signal, may detect a dicrotic notch position based on a local maximum point and a local minimum point of the second-order derivative signal of the PPG signal, may obtain a first value and a second value from both sections divided based on the dicrotic notch, may obtain a pulse pressure feature value based on the first value and the second value, and may estimate blood pressure based on the pulse pressure feature value.

Further, a display may be mounted on a front surface of the main body 710. The display may display a pulse pressure estimation result, a blood pressure estimation result, and the like. In this case, the display may have a touch screen for receiving touch input.

In addition, the main body 710 may include a storage which stores a variety of reference information for estimating pulse pressure or blood pressure, and/or processing results of the processor.

In addition, the main body 710 may include a manipulator 740 which may be provided on a side surface of the main body 710, and receives a user's control command and transmits the received control command to the processor. The manipulator 740 may have a power button to input a command to turn on/off the wearable device 700. In addition, the manipulator 740 may include a PPG sensor for acquiring a PPG signal from a finger when the finger comes into contact with the sensor.

Moreover, the main body 710 may include a communicator (or a communication interface or communication circuitry) for transmitting and receiving data with an external device. The communicator may communicate with the external device, e.g., a user's smartphone, a cuff pulse pressure measuring device, a cuff blood pressure measuring device, etc., to transmit and receive various data related to estimating pulse pressure or blood pressure.

Figure 8:
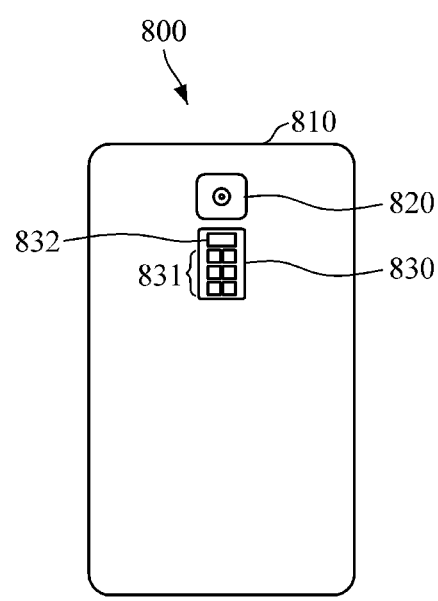
FIG. 8 is a diagram illustrating a smart device according to an example embodiment.

FIG. 8 is a diagram illustrating a smart device according to an example embodiment. In this case, the smart device 800 may include a smartphone, a tablet PC, and the like. The smart device 800 may include various embodiments of the aforementioned apparatuses 100 and 200 for estimating blood pressure.

Referring to FIG. 8, the smart device 800 includes a main body 810 and a sensor 830 mounted on a rear surface of the main body 810. For example, the sensor 830 may include a light source 831 and a detector 832. As illustrated in FIG. 8, the sensor 830 may be mounted on the rear surface of the main body 810, but is not limited thereto. For example, the sensor 830 may be formed on a fingerprint sensor on the front surface of the smart device, on a portion of a touch panel, or on a power button or a volume button mounted on a side surface or an upper surface of the smart device, and the like.

In addition, a display may be mounted on a front surface of the main body 810. The display may display a variety of information, such as a pulse pressure estimation result, a blood pressure estimation result, guide information on a contact state, and the like.

The main body 810 may include an image sensor 820 as illustrated in FIG. 8. When a user's finger approaches the sensor 830 to measure a pulse wave signal, the image sensor 820 may capture an image of the finger and may transmit the captured image to the processor. In this case, based on the image of the finger, the processor may identify a relative position of the finger with respect to an actual position of the sensor 830, and may provide guide information on the relative position of the finger to the user through the display.

As described above, the processor may estimate pulse pressure or blood pressure by using the measured PPG signal and the second-order derivative signal of the PPG signal. As described above, by considering physiological and biomechanical characteristics of blood vessels using the PPG signal and the second-order derivative signal of the PPG signal, the processor may estimate pulse pressure, MAP, SBP, or DBP more accurately. A detailed description thereof will be omitted.

The example embodiments of the disclosure may be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium may be distributed over a plurality of computer systems connected to a network so that a computer-readable code is written thereto and executed therefrom in a decentralized manner. Functional programs, codes, and code segments needed for realizing the disclosure nay be readily deduced by programmers of ordinary skill in the art to which the disclosure pertains.

At least one of the components, elements, modules or units (collectively "components" in this paragraph) represented by a block in the drawings may be embodied as various numbers of hardware, software and/or firmware structures that execute respective functions described above, according to an example embodiment. According to example embodiments, at least one of these components may use a direct circuit structure, such as a memory, a processor, a logic circuit, a look-up table, etc. that may execute the respective functions through controls of one or more microprocessors or other control apparatuses. Also, at least one of these components may be specifically embodied by a module, a program, or a part of code, which contains one or more executable instructions for performing specified logic functions, and executed by one or more microprocessors or other control apparatuses. Further, at least one of these components may include or may be implemented by a processor such as a central processing unit (CPU) that performs the respective functions, a microprocessor, or the like. Two or more of these components may be combined into one single component which performs all operations or functions of the combined two or more components. Also, at least part of functions of at least one of these components may be performed by another of these components. Functional aspects of the above exemplary embodiments may be implemented in algorithms that execute on one or more processors. Furthermore, the components represented by a block or processing steps may employ any number of related art techniques for electronics configuration, signal processing and/or control, data processing and the like.

The disclosure has been described herein with regard to preferred embodiments. However, it will be obvious to those skilled in the art that various changes and modifications can be made without changing technical conception and essential features of the disclosure. Thus, it is clear that the above-described embodiments are illustrative in all aspects and are not intended to limit the disclosure.

What is claimed is:

1. An apparatus for estimating a blood pressure, the apparatus comprising:
a sensor configured to obtain a photoplethysmogram (PPG) signal from an object; and
a processor configured to:
detect a position of a dicrotic notch based on a local maximum point and a local minimum point of a second-order derivative signal of the PPG signal;
obtain a first value and a second value from a first section and a second section of the PPG signal divided based on the dicrotic notch of the PPG signal;
estimate a pulse pressure based on a variation in a pulse pressure feature value compared to a reference pulse pressure feature value obtained at a calibration time, the pulse pressure feature value being obtained based on a ratio, between the first value and the second value;
extract a mean arterial pressure (MAP) feature value from the PPG signal, and estimate an MAP based on the extracted MAP feature value; and
estimate a blood pressure by estimating a systolic blood pressure (SBP) as shown in the following Equation 1 or estimating a diastolic blood pressure (DBP) as shown in the following Equation 2:

$$SBP\_est = \Delta MAP\_est + (1-k)\Delta PP\_est + SBP\_cal \quad \text{[Equation 1]}$$

$$DBP\_est = \Delta MAP\_est - k \times \Delta PP\_est + DBP\_cal \quad \text{[Equation 12]}$$

wherein $\Delta MAP\_est$ denotes a variation in the estimated MAP compared to a reference MAP value at the calibration time, $\Delta PP\_est$ denotes a variation in the estimated pulse pressure compared to a reference pulse pressure at the calibration time, $SBP\_cal$ denotes a reference SBP value at the calibration time, and $DBP\_cal$ denotes a reference DBP value at the calibration time.

2. The apparatus of claim 1, wherein the processor is further configured to determine pairs of local maximum points and local minimum points of the second-order derivative signal of the PPG signal, and detect the position of the dicrotic notch based on, for each pair of the pairs of the local maximum points and the local minimum points, a difference between a second-order derivative value at the local maximum point and a second-order derivative value at the local minimum point.

3. The apparatus of claim 2, wherein the processor is further configured to detect, as the position of the dicrotic notch, a time point of a local maximum point of a pair, having a largest difference between the second-order derivative value at the local maximum point and the second-order derivative value at the local minimum point.

4. The apparatus of claim 2, wherein the processor is further configured to control to request a user to remeasure the PPG signal, based on a number of the determined pairs of the local maximum points and the local minimum points of the second-order derivative signal of the PPG signal being less than or equal to a predetermined number, or based on a largest difference between the second-order derivative value at the local maximum point and the second-order derivative value at the local minimum point among the pairs of the local maximum points and the local minimum points being less than or equal to a threshold value.

5. The apparatus of claim 1, wherein the processor is further configured to determine, as a reference time, at least one of a period of the PPG signal, or a time from a start point of the period of the PPG signal to a first local minimum point of the second-order derivative signal of the PPG signal, and set a time range to detect the position of the dicrotic notch based on the determined reference time.

6. The apparatus of claim 5, wherein the processor is further configured to set a start point of the time range to a value, obtained by multiplying the reference time by a first constant, and set an end point of the time range to a value, obtained by multiplying the reference time by a second constant.

7. The apparatus of claim 1, wherein the first value and the second value comprise at least one of an area of the PPG signal in each corresponding section, a measurement time of each corresponding section, amplitude data of the PPG signal in each corresponding section, or an intensity of an nth order derivative signal of the PPG signal in each corresponding section, n being an integer equal to or greater than 1.

8. The apparatus of claim 7, wherein the first value and the second value comprise the amplitude data of the PPG signal, the amplitude data comprising at least one of a maximum amplitude value of the PPG signal in each corresponding section, a mean amplitude value of the PPG signal in each corresponding section, or a maximum value or a mean value of values obtained by raising PPG signal amplitudes to a power of n in each corresponding section.

9. The apparatus of claim 7, wherein the first value and the second value comprise the intensity of the nth order derivative signal of the PPG signal, which is a sum of absolute amplitude values in the nth order derivative signal of the PPG signal in each corresponding section.

10. An apparatus for estimating a blood pressure, the apparatus comprising:
a sensor configured to obtain a photoplethysmogram (PPG) signal from an object; and
a processor configured to:
detect a position of a dicrotic notch based on a local maximum point and a local minimum point of a second-order derivative signal of the PPG signal;
obtain a first value and a second value from a first section and a second section of the PPG signal divided based on the dicrotic notch of the PPG signal;
obtain a pulse pressure feature value based on a ratio between the first value and the second value; and
estimate a blood pressure by estimating a systolic blood pressure (SBP) as shown in the following Equation 1 or estimating a diastolic blood pressure (DBP) as shown in the following Equation 2:

$$\text{SBP\_}est = a \times \Delta feat\_CO + b \times \Delta feat\_TPR + c \times \Delta feat\_PP + d \times \text{SBP\_}cal \quad \text{[Equation 1]}$$

$$\text{DBP\_}est = a \times \Delta feat\_CO + b \times \Delta feat\_TPR + c \times \Delta feat\_PP + d \times \text{DBP\_}cal \quad \text{[Equation 2]}$$

wherein $\Delta feat\_PP$ denotes a variation in the obtained pulse pressure feature value compared to a reference pulse pressure feature value obtained at a calibration time, $\Delta feat\_CO$ denotes a variation in a cardiac output (CO) feature value compared to a reference CO feature value obtained at the calibration time, $\Delta feat\_TPR$ denotes a variation in a total peripheral resistance (TPR) feature value compared to a reference TPR feature value obtained at the calibration time, SBP_cal denotes a reference SBP value at the calibration time, and DBP_cal denotes a reference DBP value at the calibration time.

11. A method of estimating blood pressure, the method comprising:
measuring a photoplethysmogram (PPG) signal from an object;
obtaining a second-order derivative signal of the PPG signal;
detecting a position of a dicrotic notch based on a local maximum point and a local minimum point of the second-order derivative signal of the PPG signal;
obtaining a first value and a second value from a first section and a second section of the PPG signal divided based on the dicrotic notch of the PPG signal;
obtaining a pulse pressure feature value based on a ratio between the first value and the second value; and
estimating a blood pressure by estimating a systolic blood pressure (SBP) as shown in the following Equation 1 or estimating a diastolic blood pressure (DBP) as shown in the following Equation 2:

$$\text{SBP\_}est = a \times \Delta feat\_CO + b \times \Delta feat\_TPR + c \times \Delta feat\_PP + d \times \text{SBP\_}cal \quad \text{[Equation 1]}$$

$$\text{DBP\_}est = a \times \Delta feat\_CO + b \times \Delta feat\_TPR + c \times \Delta feat\_PP + d \times \text{DBP\_}cal \quad \text{[Equation 2]}$$

wherein $\Delta feat\_PP$ denotes a variation in the obtained pulse pressure feature value compared to a reference pulse pressure feature value obtained at a calibration time, $\Delta feat\_CO$ denotes a variation in a cardiac output (CO) feature value compared to a reference CO feature value obtained at the calibration time, $\Delta feat\_TPR$ denotes a variation in a total peripheral resistance (TPR) feature value compared to a reference TPR feature value obtained at the calibration time, SBP_cal denotes a reference SBP value at the calibration time, and DBP_cal denotes a reference DBP value at the calibration time.

12. The method of claim 11, wherein the detecting the position of the dicrotic notch comprises:
determining pairs of local maximum points and local minimum points of the second-order derivative signal of the PPG signal; and
detecting the position of the dicrotic notch based on, for each pair of the pairs of the local maximum points and the local minimum points, a difference between a second-order derivative value at the local maximum point and a second-order derivative value at the local minimum point.

13. The method of claim 12, wherein the detecting the position of the dicrotic notch comprises detecting, as the position of the dicrotic notch, a local maximum point of a pair, having a largest difference between the second-order derivative value at the local maximum point and the second-order derivative value at the local minimum point.

14. The method of claim 12, further comprising:
controlling to request a user to remeasure the PPG signal, based on a number of the determined pairs of the local maximum points and the local minimum points of the second-order derivative signal of the PPG signal being less than or equal to a predetermined number, or based on a largest difference between the second-order derivative value at the local maximum point and the second-order derivative value at the local minimum point among the pairs of the local maximum points and the local minimum points being less than or equal to a threshold value.

15. The method of claim 11, further comprising determining, as a reference time, at least one of a period of the PPG signal, or a time from a start point of the period of the PPG signal to a first local minimum point of the second-order derivative signal of the PPG signal, and setting a time range to detect the position of the dicrotic notch based on the determined reference time.

\* \* \* \* \*